United States Patent [19]

Esanu

[11] Patent Number: 4,569,939
[45] Date of Patent: Feb. 11, 1986

[54] DIURETIC 6-VINYL-FURO-(3,4-C)-PYRIDINE DERIVATIVES

[75] Inventor: André Esanu, Paris, France

[73] Assignee: Societe de Conseils de Recherches et d'Applications Scientifiques, France

[21] Appl. No.: 668,399

[22] Filed: Nov. 5, 1984

[30] Foreign Application Priority Data

Nov. 16, 1983 [GB] United Kingdom ............... 8330517

[51] Int. Cl.$^4$ ................. A61K 31/435; C07D 491/048
[52] U.S. Cl. ..................................... 514/302; 546/116
[58] Field of Search ......................... 546/116; 514/302

[56] References Cited

PUBLICATIONS

Strietweiser, Jr. et al., *Introduction to Organic Chemistry*, MacMillan Pub. (1976), pp. 388–389.
Garay et al., *Biochem. Pharmacol.*, 1984, 33(13), 2013–20; Chem. Abs. 101:122749a.

*Primary Examiner*—Richard A. Schwartz
*Attorney, Agent, or Firm*—Lucas & Just

[57] ABSTRACT

This invention relates to new 1,3-dihydro-6-vinyl-7-hydroxy-furo-(3,5-c)-pyridine derivatives of the general formula:

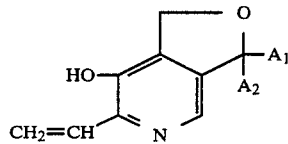

wherein each of $A_1$ and $A_2$ independently represents various hydrocarbon substituents, to a process for the preparation of these compounds from the corresponding 7-chloromethyl derivative and to pharmaceutical composition containing them. The compounds are useful as diuretics.

3 Claims, No Drawings

DIURETIC 6-VINYL-FURO-(3,4-C)-PYRIDINE DERIVATIVES

This invention relates to 6-vinyl-furo-(3,4-c)-pyridine derivatives and to a process for their preparation and to pharmaceutical compositions containing them.

The invention provides 1,3-dihydro-6-vinyl-7-hydroxy-furo-(3,4-c)-pyridine derivatives of the general formula:

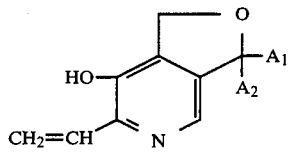

wherein each of $A_1$ and $A_2$ independently represents a hydrogen atom, a straight chain saturated or unsaturated hydrocarbon group having from 1 to 5 carbon atoms, a heterocyclic group having up to 6 ring atoms, a carbomonocyclic group, a phenylalkyl group or a phenylalkenyl group, each of the groups represented by $A_1$ and $A_2$ being unsubstituted or being substituted by one or more chlorine or fluorine atoms, trifluoromethyl groups, alkyl groups having from 1 to 5 carbon atoms, alkoxy groups having from 1 to 5 carbon atoms, alkylthio groups having from 1 to 5 carbon atoms, dialkylamino groups in which each alkyl group has from 1 to 5 carbon atoms, dialkylaminoalkoxy groups in which each of the two alkyl groups and the alkoxy group has from 1 to 5 carbon atoms or α- or β-alkoxy-N-pyrrolidinyl groups in which the alkoxy group has from 1 to 5 carbon atoms; and further provides pharmaceutically acceptable salts of such compounds.

The compounds according to the invention are of interest for their therapeutical activity, principally in the fields of selective diuresis: their administration leads to a low $K^+$ elimination associated with a high $Na^+$ elimination and a uricosuric action.

The invention provides also a process for the preparation of the said compounds comprising reacting one mole of 6-chloromethyl-7-benzoxy derivative of the formula II:

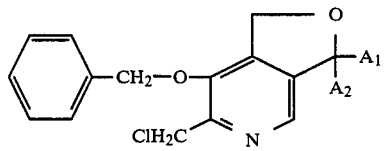

wherein $A_1$ and $A_2$ have the above meanings with one mole of triphenyl phosphine and two moles of formaldehyde at the boil, in a polar solvent such as an alkanol which leads to the desired substitution in position 6, followed by an acidic treatment, to turn the 7-benzoxy substitution to a 7-hydroxy one.

The invention further provides a pharmaceutical composition comprising a 1,3-dihydro-6-vinyl-7-hydroxy-furo-(3,4-c)-pyridine derivative of the general formula I as defined above or a pharmaceutically acceptable salt thereof in admixture with a pharmaceutically acceptable diluent or carrier.

For the obtention of the 6-chloromethyl-7-benzoxy derivative the starting material is the compound 1,3-dihydro 3-$A_1$-3-$A_2$-6-methyl-7-hydroxy-furo-(3,4-c)-pyridine obtained by the method described in previous U.S. Pat. No. 4,383,998 and U.S. patent application Ser. No. 593,700 submitted to the following sequence of reactions:

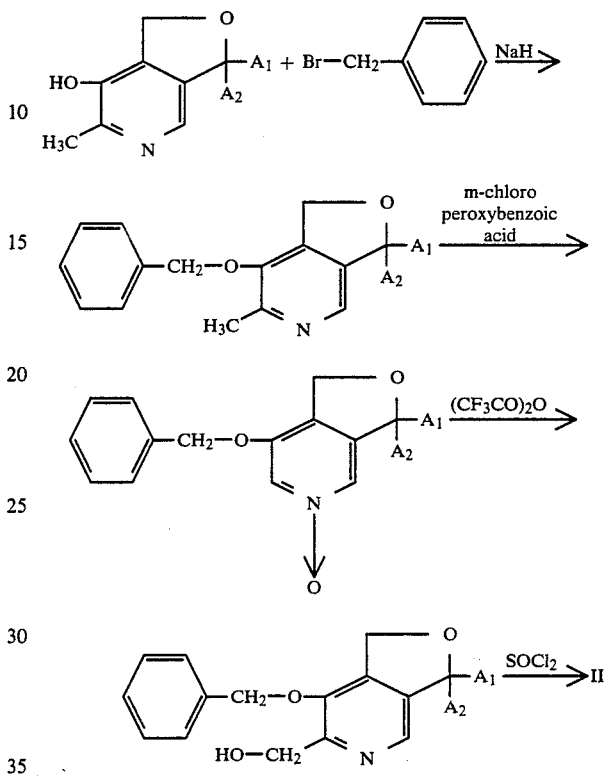

A-Preparation of the starting material

This preparation of only one of the starting compounds, the 1,3-dihydro-3-p-chlorophenyl-6-chloromethyl-7-benzoxy-furo-(3,4-c)-pyridine, is now described in detail, other starting materials being obtained by the same way.

(a) Into a one liter reactor fitted with stirring, warming and cooling means, there was poured 400 ml of dimethylformamide 12.5 g of 50% sodium hydride and slowly, under stirring, 38 g of 1,3-dihydro-3-p-chlorophenyl-6-methyl-7-hydroxy-furo-(3,4-c)-pyridine. After stirring for 90 minutes at room temperature there were added 16 ml of benzyl bromide and the resultant suspension was stirred overnight. After evaporation to dryness, the pasty product obtained was stirred with one liter of methylene dichloride, washed with water until chlorine and bromine were completely eliminated and dried on anhydrous sodium sulphate. The methylene dichloride was evaporated off and the residue dissolved in isopropanol at the boil, treated by carbon black and warm filtered, then recrystallized; it was finally washed with petroleum ether and dried. The yield was 33 g (74%) of 1,3-dihydro-3-p-chlorophenyl-6-methyl-7-benzoxy-furo-(3,4-c)-pyridine.

(b) In the same reactor as above, 30 g of the product of the previous step were treated at 0° C., in the presence of 300 ml of methylene chloride, by 18,2 g of m-peroxybenzoic acid, added slowly. After stirring overnight at room temperature, there were added 150 ml of 10% sodium sulfite; after stirring and decantation, the product was washed by the same amount of sodium sulfite, then by 150 ml of NaHCO$_3$ at 5% (twice) and by 100 ml of water (three times) then dried by anhydrous Na$_2$SO$_4$; on evaporation to dryness there was obtained a beige precipitate which was washed by petroleum ether, filtered and dried. The yield was 28 g (90%) of 1,3-dihydro-3-p-chlorophenyl-6-methyl-7-benzoxy-furo-(3,4-c)-pyridine-N-oxide.

(c) In the same reactor as above, 28 g of the compound obtained in the previous step were treated at 0°–5° C., in the presence of 175 ml of methylene dichloride, by 4.3 ml of trifluoracetic anhydride added dropwise under stirring. The mixture was stirred overnight at room temperature, then cooled and treated dropwise by 95 ml of methanol. After evaporation to dryness, the residue was taken up by 300 ml of CHCl$_3$, washed twice by 75 ml of 10% NaHCO$_3$, three times with 100 ml of water, and dried on anhydrous Na$_2$SO$_4$. The CHCl$_3$ was evaporated off and the residue washed by diethyl ether and dried under reduced pressure. The yield was 25 g (89%) of 1,3-dihydro-3-p-chlorophenyl-6-hydroxy-methyl-7-benzoxy-furo-(3,4-c)-pyridine.

(d) Into a two liter reactor fitted as above and under a nitrogen circulation, 25 g of the previously obtained compound were stirred with 0,4 l of dry benzene; there were thus slowly added 6,3 ml of SOCl$_2$ under stirring at room temperature. The mixture was warmed at 70° C. for one hour, leading to a yellow precipitate. This was separated off, washed by benzene, then by diethyl ether, and dissolved in 0.4 l of CH$_2$Cl$_2$. The solution was washed by 10% NaHCO$_3$ until pH 8, washed with water, treated by carbon black, filtered, and concentrated up to crystallization. The product was separated off, washed by diethyl ether and dried, giving 25 g (yield 92%) of 1,3-dihydro-3-p-chlorophenyl-6-chloromethyl-7-benzoxy-furo-(3,4-c)-pyridine.

B-Preparation of the compounds of the invention

EXAMPLE 1

1,3-dihydro-3-methyl-6-vinyl-7-hydroxy-furo-(3,4-c)-pyridine

Using the same apparatus as above, 14.5 g (0.05 mole) of 1,3-dihydro-3-methyl-6-chloromethyl-7-benzoxy-furo-(3,4-c)-pyridine dissolved in 300 ml of absolute ethanol were refluxed with 13.1 g (0.05 mole) of triphenyl phosphine for two hours. There were thus added 3 g (0.1 mole) of trioxymethylene then, dropwise, a solution of 2,3 g of sodium in 100 ml of methanol. At the end of the addition, the mixture was refluxed for two hours, then treated by 3 ml of acetic acid and evaporated to dryness. The dry residue was dissolved in benzene and passed through a silica gel column (eluent:-benzene). The fractions containing the 1,3-dihydro-3-methyl-6-vinyl-7-benzoxy-furo-(3,4-c)-pyridine were gathered, evaporated to dryness and retreated by isopentane. The yield was 7.35 g (55%).

This compound was then treated by 70 ml of hydrochloric acid (d 1.18) and 50 ml of ethanol under stirring at 70° C. for 3 hours.

After cooling, separation and washing (ethanol then water) there were obtained 5.1 g (87%) of 1,3-dihydro-3-methyl-6-vinyl-7-hydroxy-furo-(3,4-c)-pyridine melting at 237°–238° C. (Tottoli), the analysis of which showed a perfect correspondence with the formula C$_{10}$H$_{11}$NO$_2$, HCl. The overall yield of this sequence of reactions was 48%.

EXAMPLE 2

1,3-dihydro-3-propyl-6-vinyl-7-hydroxy-furo-(3,4-c)-pyridine

The method of example 1 was repeated, but starting with 0.1 mole of 1,3-dihydro-3-propyl-6-chloromethyl-7-benzoxy-furo-(3,4-c)-pyridine. The yield was 11 g (46%) of a product melting at 230°–232° C. (Tottoli), the analysis of which showed a good correspondence with the formula C$_{12}$H$_{15}$NO$_2$, HCl.

EXAMPLE 3

1,3-dihydro-3-cyclohexyl-6-vinyl-7-hydroxy-furo-(3,4-c)-pyridine

The method of example 1 was repeated, but starting with 0.1 mole of 1,3-dihydro-3-cyclohexyl-6-chloromethyl-7-benzoxy-furo-(3,4-c)-pyridine. The yield was 14.5 g (52%) of a product melting at 207° C. (Tottoli), the analysis of which showed a a perfect correspondence with the formula C$_{15}$H$_{19}$NO$_2$, HCl.

EXAMPLE 4

1,3-dihydro-3-phenyl-6-vinyl-7-hydroxy-furo-(3,4-c)-pyridine

The method of example 1 was repeated, but starting with 0.1 mole of 1,3-dihydro-3-phenyl-6-chloromethyl-7-benzoxy-furo-(3,4-c)-pyridine.

The yield was 12.25 g (45%) of a product melting at 241°–243° C. (Tottoli), the analysis of which showed a good correspondence with the formula C$_{15}$H$_{13}$NO$_2$, HCl.

EXAMPLE 5

1,3-dihydro-3-p-chlorophenyl-6-vinyl-7-hydroxy-furo-(3,4-c)-pyridine

The method of example 1 was repeated, but starting with 0.1 mole of 1,3-dihydro-3-p-chlorophenyl-6-chloromethyl-7-benzoxy-furo-(3,4-c)-pyridine.

The yield was 16.6 g (54%) of a product melting at 218°–221° C. (Tottoli), the analysis of which showed a good correspondence with the formula C$_{15}$H$_{12}$NO$_2$Cl, HCl.

EXAMPLE 6

1,3-dihydro-3-p-fluorophenyl-6-vinyl-7-hydroxy-furo-(3,4-c)-pyridine

The method of example 1 was repeated, but starting with 0.1 mole of 1,3-dihydro-3-p-fluorophenyl-6-chloromethyl-7-benzoxy-furo-(3,4-c)-pyridine.

The yield was 17.2 g (58%) of a product melting at 187° C. (Tottoli), the analysis of which showed a good correspondence with the formula C$_{15}$H$_{12}$NO$_2$F, HCl.

EXAMPLE 7

1,3-dihydro-3-α-furyl-6-vinyl-7-hydroxy-furo-(3,4-c)-pyridine

The method of example 1 was repeated, but starting with 0.1 mole of 1,3-dihydro-3-α-furyl-6-chloromethyl-7-benzoxy-furo-(3,4-c)-pyridine.

The yield was 12.15 g (47%) of a product melting at 210° C. (Tottoli), the analysis of which showed a good correspondence with the formula C$_{13}$H$_{11}$NO$_3$, HCl.

EXAMPLE 8

1,3-dihydro-3-p-methoxyphenyl-6-vinyl-7-hydroxy-furo-(3,4-c)-pyridine

The method of example 1 was repeated, but starting with 0.1 mole of 1,3-dihydro-3-p-methoxyphenyl-6-chloromethyl-7-benzoxy-furo-(3,4-c)-pyridine.

The yield was 13 g (43%) of a product melting at 189°–191° C. (Tottoli), the analysis of which showed a good correspondence with the formula $C_{16}H_{15}NO_3$, HCl.

EXAMPLE 9

1,3-dihydro-3,3-dimethyl-6-vinyl-7-hydroxy-furo-(3,4-c)-pyridine

The method of example 1 was repeated, but starting with 1,3-dihydro-3,3-dimethyl-6-chloromethyl-7-benzoxy-furo-(3,4-c)-pyridine.

The yield was 11.8 g (52%) of a product melting at 246°–248° C. (Tottoli), the analysis of which showed a perfect correspondence with the formula $C_{11}H_{13}NO_2$, HCl.

EXAMPLE 10

1,3-dihydro-3-methyl-3-n-pentyl-6-vinyl-7-hydroxy-furo-(3,4-c)-pyridine

The method of example 1 was repeated, but starting with 1,3-dihydro-3-methyl-3-n-pentyl-6-chloromethyl-7-benzoxy-furo-(3,4-c)-pyridine.

The yield was 14.40 g (51%) of a product melting at 245° C. (Tottoli), the analysis of which showed a perfect correspondence with the formula $C_{15}H_{21}NO_2$, HCl.

EXAMPLE 11

1,3-dihydro-3-methyl-3-p-chlorphenyl-6-vinyl-7-hydroxy-furo-(3,4-c)-pyridine

The method of example 1 was repeated, but starting with 1,3-dihydro-3-methyl-3-p-chlorophenyl-6-chloromethyl-7-benzoxy-furo-(3,4-c)-pyridine.

The yield was 15.1 g (47%) of a product melting at 212° C. (Tottoli), the analysis of which showed a good correspondence with the formula $C_{17}H_{14}NO_2Cl$, HCl.

EXAMPLE 12

1,3-dihydro-3-methyl-3-p-fluorophenyl-6-vinyl-7-hydroxy-furo-(3,4-c)-pyridine

The method of example 1 was repeated, but starting with 1,3-dihydro-3-methyl-3-p-fluorophenyl-6-chloromethyl-7-benzoxy-furo-(3,4-c)-pyridine.

The yield was 16.2 g (53%) of a product melting at 222° C. (Tottoli), the analysis of which showed a perfect correspondence with the formula $C_{17}H_{14}NO_2F$, HCl.

EXAMPLE 13

1,3-dihydro-3-ethyl-3-p-chlorophenyl-6-vinyl-7-hydroxy-furo-(3,4-c)-pyridine

The method of example 1 was repeated, but starting with 1,3-dihydro-3-ethyl-3-p-chlorophenyl-6-chloromethyl-7-benzoxy-furo-(3,4-c)-pyridine.

The yield was 14.8 g (44%) of a product melting at 199°–201° C. (Tottoli), the analysis of which showed a good correspondence with the formula $C_{18}H_{16}NO_2Cl$, HCl.

EXAMPLE 14

1,3-dihydro-3,3-diphenyl-6-vinyl-7-hydroxy-furo-(3,4-c)-pyridine

The method of example 1 was repeated, but starting with 1,3-dihydro-3,3-diphenyl-6-chloromethyl-7-benzoxy-furo-(3,4-c)-pyridine.

The yield was 17.15 g (49%) of a product melting at 206°–208° C. (Tottoli), the analysis of which showed a good correspondence with the formula $C_{21}H_{17}NO_2$, HCl.

EXAMPLE 15

1,3-dihydro-3,3-di-α-furyl-6-vinyl-7-hydroxy-furo-(3,4-c)-pyridine

The method of example 1 was repeated, but starting with 1,3-dihydro-3,3-di-α-furyl-6-chloromethyl-7-benzoxy-furo-(3,4-c)-pyridine.

The yield was 13.7 g (42%) of a product melting at 184°–186° C. (Tottoli), the analysis of which showed a good correspondence with the formula $C_{17}H_{21}NO_4$, HCl.

EXAMPLE 16

1,3-dihydro-3-cyclohexyl-3-(2,3-dichlorophenyl)-6-vinyl-7-hydroxy-furo-(3,4-c)-pyridine The method of example 1 was repeated, but starting with 1,3-dihydro-3-cyclohexyl-3-(2,3-dichlorophenyl)-6-chloromethyl-7-benzoxy-furo-(3,4-c)-pyridine.

The yield was 16.15 g (38%) of a product melting at 179°–182° C. (Tottoli), the analysis of which showed a good correspondence with the formula $C_{21}H_{21}NO_2Cl_2$, HCl.

TOXICITY

Acute toxicity has been determined by the usual routes per os and IP on mice. LD 50 per os and IP were over 600 mg/kg for all compounds.

PHARMACOLOGY

Diuretic action has been appreciated on rats (male WISTAR) weighing 180–200 g by the following method.

Rats to be treated were submitted to a complete fast for 16 hours and placed in metabolic cages wherein the urines might be collected. The rats received 2.5 ml/kg of physiologic serum per os for controls or the same volume of serum containing, in solution or in suspension, about 10 mg/kg of the tested compounds. Urines were collected after 6 hours and $Na^+$, $K^+$ and uric acid dosed. Six compounds were tested (identified by the no. of the example). For the experiments, seven batches of each eight rats were used, one for control and the six other for compounds. The results are reported in the following table wherein the figures are, in each case, the average values of the corresponding batch. Each is accompanied by the percentage of increase with respect to control.

PRESENTATION-POSOLOGY

Preferred oral forms for human use include tablets or gelatine capsules containing each 50 mg of active ingredient in admixture with appropriate excipient and/or carrier. Daily dose in human therapy is from 50 to 200 mg.

|  | Control | EX 1 | EX 5 | EX 6 | EX 7 | EX 15 | EX 16 |
|---|---|---|---|---|---|---|---|
| Per os dose mg/kg | — | 9.7 | 10.1 | 10.0 | 9.9 | 9.8 | 10.3 |
| V ml (6 h) | 0.56 | 1.33 + 137% | 1.60 + 185% | 1.92 + 243% | 1.58 + 172% | 1.18 + 111% | 1.02 + 82% |
| $Na^+$ $10^{-3}$ mEq (6 h) | 93 | 253.0 + 172% | 298.5 + 221% | 285.0 + 206% | 330.0 + 255% | 246.5 + 165% | 298.0 + 220% |
| $K^+$ $10^{-3}$ mEq (6 h) | 76 | 83.0 + 8.5% | 86.5 + 14% | 77.0 + 1.3% | 90.5 + 19% | 83.5 + 11% | 77.5 + 2% |
| $Na^+/K^+$ | 1.24 | 3.05 | 3.45 | 3.70 | 3.65 | 2.95 | 3.85 |
| Uric acid $10^{-3}$ mM (6 h) | 1.77 | 3.12 + 76% | 3.33 + 88% | 2.81 + 59% | 2.66 + 50% | 3.15 + 78% | 2.90 + 64% |

I claim:

1. A 1,3-dihydro-6-vinyl-7-hydroxy-furo-(3,4-c)-pyridine derivative of the formula:

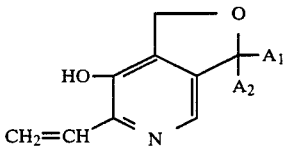

wherein each of $A_1$ and $A_2$ independently represents a hydrogen atom, a straight chain saturated or unsaturated hydrocarbon group having from 1 to 5 carbon atoms, a heterocyclic group which is an unsaturated 5-membered ring wherein the heteroatom is oxygen or sulfur, a monocycloloweralkyl or phenyl group, a phenylloweralkyl group or a phenylloweralkenyl group, each of the groups represented by $A_1$ and $A_2$ being unsubstituted or being substituted by one or more chlorine or fluorine atoms, trifluoromethyl groups, alkyl groups having from 1 to 5 carbon atoms, alkoxy groups having from 1 to 5 carbon atoms, alkylthio groups having from 1 to 5 carbon atoms, dialkylamino groups in which each alkyl group has from 1 to 5 carbon atoms, dialkylaminoalkoxy groups in which each of the two alkyl groups and the alkoxy group has from 1 to 5 carbon atoms or α- or β-alkoxy-N-pyrrolidinyl groups in which the alkoxy group has from 1 to 5 carbon atoms; or a pharmaceutically acceptable salt of such a compound.

2. A pharmaceutical composition comprising a diuretically effective amount of a 1,3-dihydro-6-vinyl-7-hydroxy-furo-(3,4-c)-pyridine derivative of the formula:

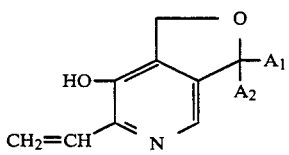

wherein each of $A_1$ and $A_2$ independently represents a hydrogen atom, a straight chain saturated or unsaturated hydrocarbon group having from 1 to 5 carbon atoms, a heterocyclic group which is an unsaturated 5-membered ring wherein the heteroatom is oxygen or sulfur, a monocycloloweralkyl or phenyl group, a phenylloweralkyl group or a phenylloweralkenyl group, each of the groups represented by $A_1$ and $A_2$ being unsubstituted or being substituted by one or more chlorine or fluorine atoms, trifluoromethyl groups, alkyl groups having from 1 to 5 carbon atoms, alkoxy groups having from 1 to 5 carbon atoms, alkylthio groups having from 1 to 5 carbon atoms, dialkylamino groups in which each alkyl group has from 1 to 5 carbon atoms, dialkylaminoalkoxy groups in which each of the two alkyl groups and the alkoxy group has from 1 to 5 carbon atoms or α- or β-alkoxy-N-pyrrolidinyl groups in which the alkoxy group has from 1 to 5 carbon atoms or a pharmaceutically acceptable salt thereof in admixture with a pharmaceutically acceptable diluent or carrier.

3. A method of achieving diuresis in a host in need of same comprising the administration of a diuretically effective amount of a 1,3-dihydro-6-vinyl-7-hydroxy-furo-(3,4-c)-pyridine derivative of the formula:

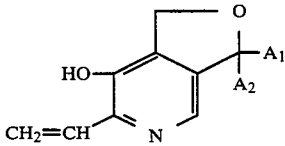

wherein each of $A_1$ and $A_2$ independently represents a hydrogen atom, a straight chain saturated or unsaturated hydrocarbon group having from 1 to 5 carbon atoms, a heterocyclic group which is an unsaturated 5-membered ring wherein the heteroatom is oxygen or sulfur, a monocycloloweralkyl or phenyl group, a phenylloweralkyl group or a phenylloweralkenyl group, each of the groups represented by $A_1$ and $A_2$ being unsubstituted or being substituted by one or more chlorine or fluorine atoms, trifluoromethyl groups, alkyl groups having from 1 to 5 carbon atoms, alkoxy groups having from 1 to 5 carbon atoms, alkylthio groups having from 1 to 5 carbon atoms, dialkylamino groups in which each alkyl group has from 1 to 5 carbon atoms, dialkylaminoalkoxy groups in which each of the two alkyl groups and the alkoxy group has from 1 to 5 carbon atoms or α- or β-alkoxy-N-pyrrolidinyl groups in which the alkoxy group has from 1 to 5 carbon atoms or a pharmaceutically acceptable salt thereof in admixture with a pharmaceutically acceptable diluent or carrier.

* * * * *